(12) United States Patent
Bombardelli

(10) Patent No.: US 8,092,844 B2
(45) Date of Patent: Jan. 10, 2012

(54) COMBINATIONS OF VASOACTIVE AGENTS AND THEIR USE IN THE TREATMENT OF SEXUAL DYSFUNCTIONS

(75) Inventor: Ezio Bombardelli, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 12/496,194

(22) Filed: Jul. 1, 2009

(65) Prior Publication Data

US 2009/0269426 A1 Oct. 29, 2009

Related U.S. Application Data

(62) Division of application No. 10/563,980, filed as application No. PCT/EP2004/007374 on Jul. 6, 2004, now abandoned.

(30) Foreign Application Priority Data

Jul. 11, 2003 (IT) .............................. MI2003A1428

(51) Int. Cl.
*A61K 36/16* (2006.01)
*A61K 36/00* (2006.01)

(52) U.S. Cl. ...................................... 424/752; 424/725

(58) Field of Classification Search ........................ None
See application file for complete search history.

(56) References Cited

U.S. PATENT DOCUMENTS

| 5,376,371 | A | 12/1994 | Bombardelli |
| 5,665,335 | A * | 9/1997 | Bombardelli et al. ........ 424/70.1 |
| 6,306,841 | B1 * | 10/2001 | Place et al. ..................... 514/149 |
| 6,514,536 | B2 * | 2/2003 | Drizen et al. .................. 424/486 |
| 2002/0013280 | A1 * | 1/2002 | Xin ................................. 514/27 |
| 2002/0034557 | A1 | 3/2002 | Crosby et al. |
| 2003/0008020 | A1 | 1/2003 | Adams et al. |

FOREIGN PATENT DOCUMENTS

| EP | 0 304 603 | | 1/1989 |
| EP | 304603 | A1 * | 3/1989 |
| EP | 0 418 806 | | 3/1991 |
| EP | 0692250 | A2 * | 7/1994 |
| EP | 0 692 250 | | 1/1996 |
| EP | 0 693 278 | A | 1/1996 |
| JP | 09-157136 | A | 6/1997 |

OTHER PUBLICATIONS

Medscape Medical News. New Approaches to Female Sexual Arousal Disorder. Jun. 3, 2002. Retrieved from the internet. <http://www.medscape.com/viewarticle/434478>. Retrieved on Apr. 28, 2010. pp. 1-2.*
Drewes et al. Recent Findings on Natural Products With Erectile-Dysfunction Activity. Phytochemistry. 62. Apr. 2003. pp. 1019-1025.*
Drewes Siegfried E et al.:"Recent findings on natural products with erectile-dysfunction activity." Phytochemistry. Apr. 2003, vol. 62, No. 7, Apr. 2003, pp. 1019-1025, XP004410106 ISSN: 0031-9422 p. 1022, col. 2.

* cited by examiner

*Primary Examiner* — Melenie McCormick
(74) *Attorney, Agent, or Firm* — Young & Thompson

(57) ABSTRACT

This invention relates to combinations of vasoactive substances which are useful in the treatment of sexual dysfunctions associated with poor local blood supply and/or insufficient lubrication. The active compounds are selected from a:
esculoside or visnadine;
forskolin or extracts containing it, or alternatively, purified lipophilic extracts of plants of the genus *Ipomea*;
esters of ximenynic acid;
optionally, at least one compound selected from a icarin or derivatives or extracts thereof which contain it, amentoflavone, and *Gingko biloba* dimeric flavones. The combination of these vasoactive substances is incorporated in gels and lotions designed to be applied to the genital organs. These formulations are useful in inducing erection of the male and female sex organs and enhancing orgasm and sexual performance. The formulations are particularly useful in the treatment of female sexual dysfunctions.

6 Claims, No Drawings

COMBINATIONS OF VASOACTIVE AGENTS AND THEIR USE IN THE TREATMENT OF SEXUAL DYSFUNCTIONS

CROSS REFERENCE TO RELATED APPLICATIONS

This application is a division of application Ser. No. 10/563,980 filed on Feb. 27, 2006; which is the 35 U.S.C. 371 national stage of International application PCT/EP2004/007374 filed on Jul. 6, 2004; which claimed priority to Italian application MI2003A001428 filed Jul. 11, 2003. The entire contents of each of the above-identified applications are hereby incorporated by reference.

This invention relates to combinations of vasoactive substances which are useful in the treatment of sexual dysfunctions associated with poor local blood supply and/or insufficient lubrication.

Loss of erectile capacity in men is an event which adversely affects the 5 physical, emotional and social sphere of the sufferer. When this sexual dysfunction arises, men come to expect yet another "failure" whenever they have sexual intercourse, thus generating a particular state of mind which is both cause and effect of a problem that was originally only physical.

As sexuality is an important means of communication between a couple, deterioration of erectile potency leads to a build-up of emotional tension between the two partners and a consequent deterioration in their relationship. Loss or absence of erectile capacity and lubrication to various extents also constitutes a serious problem in women, with adverse consequences on the couple's relationship. A variety of mediators and receptors are involved in the tumescence of the male and female genital organs. Acetylcholine (Ach), for example, is the best-known parasympathetic neurotransmitter. In vitro, it causes relaxation of smooth muscle striations previously contracted by noradrenaline, and contraction of smooth muscle cell isolates. This suggests that the main action of Ach is to contract the smooth muscles and determine the release of a substance which causes cavernous relaxation. In addition to Ach, the parasympathetic nerves also release other neurotransmitters, including nitric oxide (NO), VIP and CGRP (calcitonin gene-related peptide).

Nitric oxide (NO) is synthesised from L-Arginine through the action of the enzyme NOs (nitric oxide synthetase). The two sources of NO in the penis and clitoris are represented by the parasympathetic nerve endings and the endothelium, synthesised by different NOs enzymes: nNOs (neuronal NOs), which is present in the cytoplasm of the parasympathetic nerves, and eNOs (endothelial NOs), found in the endothelium of the blood vessels and trabecular tissue, which mainly seems to bond to the cell membranes. Numerous experiments have demonstrated that stimulation of the parasympathetic nerves leads to the release of NO as a result of direct action by the nerve endings (reaction catalysed by nNOs) and indirect action resulting from the effect of Ach, released by the parasympathetic nerves, on the vascular endothelium, with stimulation of eNos. There is also evidence in support of a tonic release of NO by the endothelium and the involvement of partial oxygen pressure. In fact, periods when partial oxygen tension is low, as in conditions of flaccidity, are associated with reduced NOs activity. Finally, various studies have confirmed the ability of other substances, whose physiological significance has not yet been established, to determine the release of NO by the endothelium. The clinical evidence that NO plays a part in the erection of the penis includes the observation that intracavernous injection of NO-releasing substances can produce an erection in impotent men as well as men with normal sexual potency.

The Ach released by the parasympathetic fibres bonds to muscarinic receptors present on the endothelial cell membranes and the smooth muscle cell membranes. In the endothelium, this bond promotes the activation of eNOs with subsequent release of NO and inhibition of noradrenaline (NA). Inhibition of NA release is essential to the physiology of the erection. NA, released by the sympathetic nerve endings, bonds with α1-adrenergic and clitoris are represented by the parasympathetic nerve endings and the endothelium, synthesised by different NOs enzymes: nNOs (neuronal NOs), which is present in the cytoplasm of the parasympathetic nerves, and eNOs (endothelial NOs), found in the endothelium of the blood vessels and trabecular tissue, which mainly seems to bond to the cell membranes. Numerous experiments have demonstrated that stimulation of the parasympathetic nerves leads to the release of NO as a result of direct action by the nerve endings (reaction catalysed by nNOs) and indirect action resulting from the effect of Ach, released by the parasympathetic nerves, on the vascular endothelium, with stimulation of eNos. There is also evidence in support of a tonic release of NO by the endothelium and the involvement of partial oxygen pressure. In fact, periods when partial oxygen tension is low, as in conditions of flaccidity, are associated with reduced NOs activity. Finally, various studies have confirmed the ability of other substances, whose physiological significance has not yet been established, to determine the release of NO by the endothelium. The clinical evidence that NO plays a part in the erection of the penis includes the observation that intracavernous injection of NO-releasing substances can produce an erection in impotent men as well as men with normal sexual potency.

The Ach released by the parasympathetic fibres bonds to muscarinic receptors present on the endothelial cell membranes and the smooth muscle cell membranes. In the endothelium, this bond promotes the activation of eNOs with subsequent release of NO and inhibition of noradrenaline (NA). Inhibition of NA release is essential to the physiology of the erection. NA, released by the sympathetic nerve endings, bonds with α1-adrenergic membrane receptors (in the cavernous tissue, type ca receptors outnumber type β receptors by a ratio of 10:1), leading to an increase in the activity of phospholipase C (PLC), which converts phosphatidylinositol (PIP) into inositol triphosphate (IP3) and diacylglycerol (DAG). IP3 induces the release of calcium ions from the sarcoplasmic reticulum, and DAG stimulates the enzyme protein kinase C (PKC). This enzyme, by opening the L-type calcium channels and closing the potassium channels, increases the intracytoplasmic calcium concentration, leading to contraction of the smooth muscles.

The NO released by the parasympathetic nerve endings and the endothelium is a lipophilic molecule, and therefore able to cross the smooth muscle cell membrane.

Despite its short half-life (approx. 5 seconds), after reaching the cytoplasm of the muscle cell it stimulates its receptor, the enzyme guanylate cyclase, to convert guanosine triphosphate (GTP) into the second active messenger, cyclic guanosine monophosphate (cGMP). The intracytoplasmic levels of cGMP are controlled by the extent of the nitrergic stimulus and the catabolism rate of the enzyme phosphodiesterase V (PDE). Once stimulated, cGMP activates the enzyme protein kinase G (PKG), which closes the L-type calcium channels and opens the potassium channels. VIP, like the prostanoids (PGE1), mainly acts via specific receptors on the surface of the smooth muscle cell, stimulating the enzyme adenylate cyclase (a membrane enzyme). This enzyme converts ATP into cyclic AMP (cAMP), which in turn causes a reduction in the intracellular calcium concentration and relaxation of the smooth muscles.

It has now been discovered that by associating esculoside or visnadine, icarin and derivatives or extracts which contain it, amentoflavone, dimers of *Gingko biloba*, forskolin or purified extracts of *Coleus forskolii*, purified extracts of plants of the genus *Ipomea* and esters of ximenynic acid, which modify physiologically dulled or altered parameters, and exploiting the synergic interactions between the active constituents, the functionality of the genital organs can be restored very effectively.

This invention relates in particular to combinations of vasoactive substances useful in the treatment of sexual dysfunctions associated with poor local blood supply to the male and female sex organs.

The topical compositions according to the invention contain:

esculoside or visnadine;
forskolin or extracts containing it, or alternatively, purified lipophilic extracts of plants of the genus *Ipomea*;
esters of ximenynic acid;
optionally, at least one compound selected from a icarin or derivatives or extracts thereof which contain it, amentoflavone, and *Gingko biloba* dimeric flavones.

Visnadine is a coumarin mainly found in the seeds of *Ammi visnaga*, a plant traditionally used to treat anginoid disorders. The compound has recently been used in the pharmaceutical field as a coronary dilator. We have demonstrated on various occasions that this compound, when applied topically, has a strong vasokinetic action on the precapillary arteries and arterioles, increasing the blood flow and tissue perfusion (EP 0418806). The supply of arterial blood to the erectile tissues induces the start of the erection and maintains it for as long as the compound is present in the tissues. Visnadine also has an anti-phosphodiesterase activity useful to maintain the cyclic nucleotides.

Esculoside, a coumarin glucoside present in many plants, such as *Aesculus hippocastanum*, *Fraxinus communis*, etc., possesses a vasokinetic action and venotropic activity at both venous and arterial levels.

Icarin and its derivatives act on cGMP phosphodiesterase V. High levels of cGMP are required to maintain the erection in the male and female genital organs and therefore the performance necessary for sexual intercourse. Icarin derivatives include 7-hydroxyethyl-icarin or 7-aminoethyl-icarin, 7-hydroxyethyl-3-0-ramnosyl-icarin, 7-aminoethyl-7-desgluco-3-raminosyl-icarin, 8-dihydro-icarin and its glucosides in 7 and 3, and 7-hydroxyethyl-7-desgluco-icarin.

Amentoflavone is a biflavone present in modest amounts in numerous plants, such as *Gingko biloba*, *Brakeringea zanguebarica* and *Taxus* sp. The addition of amentoflavone is particularly useful in some formulations, and is one of the subjects of this invention, because it acts as a very powerful inhibitor of phosphodiesterase and on the release of oxytocin, which is a known aphrodisiac at low doses.

Forskolin, and the extracts which contain it, is a known adenylate cyclase agonist. A purified extract of *Coleus forskolii* is particularly preferred.

Extracts of plants of the genus *Ipomea* also possess a significant activity on adenylate cyclase; the standardised lipophilic extracts of *Ipomea hederacea*, *Ipomea parassitica* and *Ipomea batatas* are particularly preferred.

The formulations according to the invention improve sensual performance, especially in women. For example, a combination in gel form containing 1% esculoside, 0.2% forskolin and 1% ethyl ximenynate was administered to a group of 10 female volunteers of child-bearing age. The efficacy test, in which the blood flow parameters in the external genital organs were instrumentally measured by a non-invasive method (Laser Doppler and optical probe videocapillaroscopy), demonstrated that the blood flow increased by up to 200% of the basal value; as regards subjective sensations, the patients reported general well-being, and sexual excitement within half an hour. In men, application of the formulations according to the invention leads to a rapid erection which is prolonged for as long as required to complete the act of sexual intercourse.

The following examples illustrate the invention.

EXAMPLE 1

| | |
|---|---|
| Esculoside | 1.00 g |
| Ethyl ximeninate | 2.00 g |
| *Coleus* purified extract > 80% | 0.20 g |
| Polyethylene 400 | 10.00 g |
| Ethoxydiglycol (TRANSCUTOL - Gattefossé) | 10.00 g |
| Caprylic/Capric PEG-6 glycerides (SOFTIGEN 767 - Huls) | 10.00 g |
| Sorbitol | 10.00 g |
| Polysorbate 20 | 8.00 g |
| Carbomer (ULTREZ 10 - BF Goodrich) | 1.00 g |
| Imidazolidinyl urea | 0.30 g |
| Xanthane gum (KELTROL TF - Kelco) | 0.30 g |
| Methyl paraben | 0.20 g |
| Disodium EDTA | 0.10 g |
| Hydroxytoluene butoxide | 0.05 g |
| 10% sol. sodium hydroxide | 2.00 g |
| Perfume (JENNY- Dragoco) | 0.01 g |
| Water | q.s. to 100 g |

EXAMPLE 2

| | |
|---|---|
| Visnadine | 1.00 g |
| Ethyl ximeninate | 2.00 g |
| *Coleus* purified extract > 80% | 0.20 g |
| polyethylene 400 | 10.00 g |
| Ethoxydiglycol (TRANSCUTOL - Gattefossé) | 10.00 g |
| Caprylic/Capric PEG-6 glycerides (SOFTIGEN 767 - Huls) | 10.00 g |
| Sorbitol | 10.00 g |
| Polysorbate 20 | 8.00 g |
| Carbomer (ULTREZ 10 - BF Goodrich) | 1.00 g |
| Imidazolidinyl urea | 0.30 g |
| Xanthane gum (KELTROL TF - Kelco) | 0.30 g |
| Methyl paraben | 0.20 g |
| Disodium EDTA | 0.10 g |
| Hydroxytoluene butoxide | 0.05 g |
| 10% sol. sodium hydroxide | 2.00 g |
| Perfume (JENNY- Dragoco) | 0.01 g |
| Water | q.s. to 100 g |

EXAMPLE 3

| | |
|---|---|
| Visnadine | 1.00 g |
| 7-hydroxyethyl-7-desgluco-icarin | 1.00 g |
| Forskolin | 0.20 g |
| Amentoflavone | 0.20 g |
| Ethyl ximeninate | 2.00 g |
| Polyethylene 400 | 10.00 g |

EXAMPLE 3

| | |
|---|---|
| Ethoxydiglycol (TRANSCUTOL - Gattefossé) | 10.00 g |
| Caprylic/Capric PEG-6 glycerides (SOFTIGEN 767 - Huls) | 10.00 g |
| Sorbitol | 10.00 g |
| Polysorbate 20 | 8.00 g |
| Carbomer (ULTREZ 10 - BF Goodrich) | 1.00 g |
| Imidazolidinyl urea | 0.30 g |
| Xanthane gum (KELTROL TF - Kelco) | 0.30 g |
| Methyl paraben | 0.20 g |
| Disodium EDTA | 0.10 g |
| Hydroxytoluene butoxide | 0.05 g |
| 10% sol. sodium hydroxide | 2.00 g |
| Perfume (JENNY- Dragoco) | 0.01 g |
| Water | q.s. to 100 g |

EXAMPLE 4

| | |
|---|---|
| Esculoside | 1.00 g |
| 7-Hydroxyethyl-7desgluco-icarin | 1.00 g |
| *Ipomea hederacea* lyophilic standardized extract | 0.20 g |
| *Gingko biloba* dimeric flavones | 0.20 g |
| Ethyl ximeninate | 1.00 g |
| Polyethylene 400 | 10.00 g |
| Ethoxydiglycol (TRANSCUTOL - Gattefossé) | 10.00 g |
| Caprylic/Capric PEG-6 glycerides (SOFTIGEN 767 - Huls) | 10.00 g |
| Sorbitol | 10.00 g |
| Polysorbate 20 | 8.00 g |
| Carbomer (ULTREZ 10 - BF Goodrich) | 1.00 g |
| Imidazolidinyl urea | 0.30 g |
| Xanthane gum (KELTROL TF - Kelco) | 0.30 g |
| Methyl paraben | 0.20 g |
| Disodium EDTA | 0.10 g |
| Hydroxytoluene butoxide | 0.05 g |
| 10% Sol. sodium hydroxide | 2.00 g |
| Perfume (JENNY- Dragoco) | 0.01 g |
| Water | q.s. to 100 g |

The invention claimed is:

1. A method for treating sexual dysfunction in humans, the method comprising topically administering an effective amount of a topical composition to a subject in need thereof, wherein the topical composition comprises:
   esculoside or visnadine;
   *Coleus forskolii* extract;
   ximenynic acid ethyl ester; and
   an icariin derivative selected from the group consisting of 7-hydroxyethyl-7-desgluco-icariin, 7-hydroxyethyl-icariin, 7-aminoethyl-icariin, 7-hydroxyethyl-3-0-rhamnosyl-icariin, 7-aminoethyl-3-rhamnosyl-icariin, 8-dihydro-icariin, or glycosides thereof.

2. The method of claim 1, wherein the composition further comprises one or more of amentoflavone, and *Gingko biloba* dimeric flavone.

3. The method of claim 1, wherein the composition further comprises lubricants and anti-irritant excipients.

4. The method of claim 1, wherein the composition comprises visnadine.

5. A method for treating sexual dysfunction in in humans, the method comprising topically administering an effective amount of a topical composition to a subject in need thereof, wherein the topical composition comprise, by weight:
   1% visnadine
   0.2% *Coleus forskolii* extract; and
   2% ximenynic acid ethyl ester.

6. The method of claim 5, wherein the topical composition further comprises, by weight:
   0.2% amentoflavone or *Gingko biloba* dimeric flavone.

* * * * *